Figure 1:
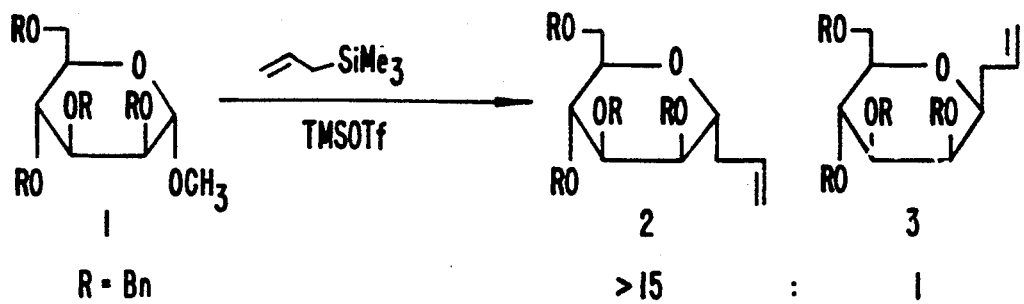

United States Patent [19]

Bednarski et al.

[11] Patent Number: 5,212,075
[45] Date of Patent: May 18, 1993

[54] COMPOSITIONS AND METHODS FOR INTRODUCING EFFECTORS TO PATHOGENS AND CELLS

[75] Inventors: Mark D. Bednarski, Berkeley; Carolyn R. Bertozzi, Albany; Jon O. Nagy, Rodeo, all of Calif.

[73] Assignee: The Regents of the University of California, Oakland, Calif.

[21] Appl. No.: 686,342

[22] Filed: Apr. 15, 1991

[51] Int. Cl.$^5$ .................. C12Q 1/00; G01N 33/53
[52] U.S. Cl. ..................... 435/72; 435/7.22; 435/7.32; 435/7.37; 514/888
[58] Field of Search ............ 435/7.2, 7.22, 7.32, 435/7.37; 514/888

[56] References Cited

U.S. PATENT DOCUMENTS

| | | | |
|---|---|---|---|
| 3,951,748 | 4/1976 | Devlin | 435/7.22 |
| 4,207,414 | 6/1980 | Kasper | 536/53 |
| 4,297,104 | 10/1981 | Claude | 436/520 |
| 4,476,119 | 10/1984 | della Valle et al. | 514/25 |
| 4,693,966 | 9/1987 | Houghton et al. | 435/7.2 |
| 4,694,076 | 9/1987 | Ogawa et al. | 535/17.2 |
| 4,698,420 | 10/1987 | Urnovitz | 530/391.9 |
| 4,844,893 | 7/1989 | Honsik et al. | 435/240.2 |
| 4,845,026 | 7/1989 | Kung et al. | 435/7.23 |
| 4,859,609 | 8/1989 | Dull et al. | 436/501 |
| 4,869,826 | 9/1989 | Wang et al. | 435/176 |
| 4,886,743 | 12/1989 | Hood et al. | 435/7.22 |
| 4,914,035 | 4/1990 | Hasegawa et al. | 536/18.6 |
| 4,918,177 | 4/1990 | Yoshimura et al. | 536/18.7 |
| 4,925,796 | 5/1990 | Bergh et al. | 435/97 |
| 4,963,653 | 10/1990 | Nagai et al. | 530/322 |
| 4,965,198 | 10/1990 | Yamasaki et al. | 435/70.21 |
| 4,981,782 | 1/1991 | Judd et al. | 530/387.9 |
| 4,990,603 | 2/1991 | Ogawa et al. | 536/17.4 |
| 5,019,387 | 5/1991 | Haynes et al. | 530/387.9 |
| 5,030,565 | 7/1991 | Niman et al. | 530/387.7 |
| 5,064,755 | 11/1991 | Howard et al. | 435/7.2 |

FOREIGN PATENT DOCUMENTS 0314317 5/1989 European Pat. Off. .

OTHER PUBLICATIONS

Shokat et al. (1991), *J. Am. Chem. Society* vol. 113: 1861-1862.
Roitt et al., "Immunology", The C. V. Mosby Company, St. Louis, Toronto, (1985) pp. 18.1, 18.14 & 18.15.
Traunecker et al., *Nature*, vol. 339, pp. 68-70 (1989).
Dennent, G. (1975) *Nature*, vol. 225 pp. 712 & 713.
Capon et al., *Nature*, vol. 332, pp. 525-531 (1989).
Capon et al., (1989) *Nature* 337:525-531.
Sharon and Lis (1989) *Science* 246:227-246.
Badger et al. (1988) *Proc. Natl. Acad. Sci. USA* 85:3304-3308.
Sauter et al. (1989) *Biochemistry* 28:8388-8396.
Whitesides (1991) *J. Am. Chem. Soc.* 113:686-687.
Crich and Lim (1990) *Tet. Lett.* 31:1897-1900.
Nicotra et al. (1987) *J. Org. Chem.* 52:5627-5630.
Hosomi et al. (1984) *Tet. Lett.* 25:2383-2386.
Norbeck et al. (1987) *J. Org. Chem.* 52:2174-2179.

*Primary Examiner*—Ronald W. Griffin
*Attorney, Agent, or Firm*—Townsend and Townsend

[57] ABSTRACT

Compositions and methods for the inhibition and prevention of pathogenic infection and neoplastic disease are provided. The compositions include hybrid molecules having a binding moiety and an effector moiety joined by a linker region. When administered to a host, the binding moiety, such as a carbohydrate, attaches to a receptor, such as a conserved lectin receptor on the pathogen or neoplastic cell, and the effector moiety provides an invariant antigenic determinant for eliciting or modulating an immune response. The effector moiety may also be a drug or other compound which inhibits growth of a bound pathogen or cell. Compositions comprising the hybrid molecule in a suitable pharmaceutical carrier are also provided.

19 Claims, 4 Drawing Sheets

COMPOSITIONS AND METHODS FOR INTRODUCING EFFECTORS TO PATHOGENS AND CELLS

This invention was made with Government support under Grant (or Contract) No. NIH 1946002123A1, awarded by the Department of Health and Human Services. The Government has certain rights in this invention.

BACKGROUND OF THE INVENTION

1. Field of the Invention

The present invention relates generally to compositions and methods for specifically targeting pathogens and cells. More particularly, the present invention relates to the use of hybrid molecules including a receptor-binding moiety and an effector moiety for altering the antigenic character of or delivering drugs to pathogens anc cells.

The primary defense mechanism of man and other vertebrates against pathogenic infection is the immune system. The immune response includes two separate pathways to deal with invasion by a foreign substance. The first pathway, referred to as the "humoral response," relies on antibody molecules to bind directly to pathogen to trigger a series of events (the complement cascade or the binding of macrophages and other leukocytes) to eliminate the pathogen from the body. The second immune pathway, referred to as the "cellular response," relies on T-cell recognition of an antigenic region on the pathogen, again leading ultimately to elimination of the pathogen from the system. Both the humoral and cellular responses thus rely on antigenic recognition of the pathogen in order to kill the pathogen and protect the host.

While the immune response is an exquisite and effective protective mechanism against a wide variety of pathogens, there are certain pathogens which evade both pathways of the immune response by changing their cell surface antigens sufficiently rapidly so that they are not recognized by the antibodies which have been elicited during earlier stages of infection. Pathogens with such an ability to evade the immune response include viruses, such as the influenza virus, papilloma viruses, picornaviruses, polyoma virus, and rhinoviruses; bacteria, such as *Escherichia coli* and *Vibrio cholerae;* and protozoa, such as *Entamoeba histolytica, Trypanosoma cruzii, Plasmodium knowlesi,* P. vivax and the like.

Most or all pathogens initiate infection by binding to a surface ligand on the cell being infected. For example, the pathogen may possess a lectin receptor which is able to specifically bind to a carbohydrate ligand on the cell to be infected. To prevent infection, it has been proposed to inhibit initial attachment of the pathogen using drugs which block binding of the pathogen to the cells which are subject to infection. While such drugs can be effective, high dosages may be required to block all available binding receptors on the pathogen. Moreover, the drugs are passive and do not enhance the killing and elimination of the pathogen from the host. Another class of blocking agents include soluble polypeptide receptors, such as soluble CD4 used to inhibit binding of HIV-1 to T-cells. The use of soluble polypeptide receptors has not generally been successful, perhaps due to degradation of the polypeptides after they are administered to a patient.

Sialic acids, derivatives of N-acetyl neuraminic acid (NeuAc), are carbohydrate groups found terminating cell-surface glycoproteins and glycolipids. Glycosides of NeuAc are often utilized by pathogens as an attachment point to cells prior to infection. The use of sialic acid analogs as drugs directed towards the influenza virus has been proposed. The use of O-linked glycosides as potential viral inhibitors, however, is severely limited because of the presence of the neuraminidase enzyme on the virus. This enzyme cleaves the glycosidic bond of NeuAc giving rise to the free sugar which does not inhibit viral attachment. Therefore, a stable non-hydrolyzable analog of sialic acid promises to be useful as an antiviral drug.

For these reasons, it would be desirable to provide improved compositions and methods for enhancing a host's immune response against pathogenic infection, particularly against pathogenic infection by organisms capable of altering their antigenic appearance over time. It would be particularly desirable to provide compositions which are able to target a pathogen and provide at least one invariant antigenic determinant so that a host's immune response can target the pathogen based on the invariant determinant. The compositions will desirably be small, preferably being less than 3 kilodaltons (kD), more preferably being less than 2 kD, and most preferably being less than 1 kD in order to increase their survival time after administration to the host. The compositions should further be substantially free from non-specific binding so that they target the immune response solely against the desired pathogenic organism. The compositions will preferably not themselves be destroyed by the immune response so that individual molecules may successively bind more than one pathogen to reduce the dosage required. It will further be desirable to administer compositions which elicit a secondary or memory response against an antigen against which the host has been previously sensitized.

2. Description of the Background Art

Soluble hybrid molecules, designated immunoadhesins, comprising the gp120-binding domain of CD4 glycoprotein attached to portions of the Fc region of IgG are described in Capon et al. (1989) Nature 337:525-531. See also European Patent Application 0 314 317. Use of the immunoadhesins for treatment of acquired immunodeficiency syndrome (AIDS) is proposed. Hybrid receptors comprising the ligand-binding domain of a receptor, such as a growth factor receptor, attached to a heterologous reporter polypeptide, such as an enzyme are described in U.S. Pat. No. 4,859,609, to Dull and Ullrich. Schultz and Shokat (1991) J. Am. Chem. Soc. 13:1861 describe the use of CD4-nitrophenol conjugates to target anti-DNP antibodies against HIV-1. Sharon and Lis (1989) Science 246:227-234 describe the nature of some pathogenic receptors (lectins) which bind to cell surface carbohydrates to initiate infection. Win compounds are described in Badger et al. (1988) Proc. Natl. Acad. Sci. 85:3304-3308. Win compounds bind to rhinoviruses and inhibit uncoating of virus (which is necessary for infection). The synthesis of sialic acid analogs intended for use as drugs is reported in Sauter et al. (1989) Biochemistry 28:8388 and Whitesides (1991) J. Am. Chem. Soc. 113:686-687.

SUMMARY OF THE INVENTION

The present invention comprises a hybrid molecule which is able to bind to a receptor, usually a conserved receptor, on a pathogen or neoplastic cell in order to introduce at least one heterologous determinant site onto the pathogen or cell surface. The hybrid molecules are small molecules, typically having molecular weights below about 3 kD, which comprise a binding moiety attached to an effector moiety capable of eliciting or modulating an immune response when administered to a host. The binding moiety preferably binds to the pathogenic or cellular receptor with an affinity of at least about 1 mM$^{-1}$ ($10^{-3}$M$^{-1}$). The binding moiety will typically mimic a carbohydrate binding region present on a host cell which binds the pathogen receptor as part of the initiation of infection or a neoplastic cell as part of the metastatic process. Usually, the binding moiety will include at least one sugar characteristic of the host cell binding ligand (usually a terminal sugar) joined to the remainder of the hybrid molecule through a carbon-linkage. Such carbon-linked sugar(s) are desirable since they are less subject to chemical and enzymatic degradation, than are natural oxygen-linked sugars. Frequently, more than one sugar from the cell surface ligand will be incorporated in the hybrid molecule. Alternatively, other small drugs and moieties capable of binding to the receptor on the pathogen or neoplastic cells, other than carbohydrates, may be employed.

The effector moiety will usually be capable of eliciting, modulating, or otherwise participating in the humoral immune response when administered to a host as part of the hybrid molecule. In particular, the effector moiety may elicit a primary immunogenic response when the host has not been previously sensitized to the antigenic determinant defined by the effector. Alternatively, and preferably, the effector moiety may elicit a secondary or memory response when the host has previously been sensitized to the corresponding antigenic determinant. In addition or as a further alternative, the effector moiety may be a drug capable of killing a bound cell, inhibiting cellular attachment, or otherwise interfering with the pathogenic or metastatic process.

The linker will be capable of covalently binding to both the binding moiety and the effector moiety and will be able to maintain the proper spacing therebetween, typically from about 10 Å to 40 Å. The linker will usually be flexible to permit relative motion between the binding moiety and the effector moiety so that the effector moiety will be sufficiently exposed on the surface of the pathogen to participate in the desired interaction with the cells of the host's immune system. The linker should be substantially free from any features which could result in non-specific binding of the hybrid molecules.

The present invention further comprises compositions containing the hybrid molecules as just described present in a pharmaceutically-acceptable carrier.

The present invention also comprises novel carbon-linked sialic acid derivatives which may be particularly useful in preparing the hybrid molecules described above.

The present invention provides methods for introducing a heterologous antigenic determinant to a pathogen or neoplastic cell by exposing the pathogen or cell to the hybrid molecules described above. The binding moiety of the hybrid molecules will specifically bind to the receptor, usually a conserved receptor, on the pathogen or cell, and the effector moiety provides an invariant determinant which can act as a target to elicit an immune response against the pathogen. The effector may also provide for direct killing of the pathogen or cell. In a particular aspect, the method can be used to treat pathogenic infection by administering the hybrid molecule to a host to elicit or modulate the host's own humoral or cellular immune response.

BRIEF DESCRIPTION OF THE DRAWINGS

FIGS. 1–4 illustrate the synthetic schemes for the preparation of carbon-linked mannose glycosides as described in the Experimental section hereinafter.

FIG. 5 is an electron micrograph showing the localization of gold particles on the surface of an *E. coli* cell. The particles were bound through a hybrid molecule consisting of a mannose binding moiety attached to biotin through a carbon linkage. Avidin, anti-avidin antibodies, and protein A labelled with the gold particles were exposed to cell and completed a bridge binding the gold particles. The location of a gold particle is shown by the arrow.

FIG. 6 is an electron micrograph showing a strain of *E. coli,* similar to that illustrated in FIG. 5, in the absence of the hybrid molecule. The cell was exposed to avidin, anti-avidin antibodies, and protein A labelled with gold particles. No localization of the gold particles was achieved without the hybrid molecules.

FIGS. 7–9 illustrate the synthetic scheme for the preparation of a carbon-linked sialic acid residue as described in the Experimental section hereinafter.

DESCRIPTION OF THE SPECIFIC EMBODIMENTS

According to the present invention, hybrid molecules include a binding moiety and an effector moiety covalently joined together by a linker region. The binding moiety is capable of specifically binding to a conserved surface receptor, typically a lectin, on a pathogen of interest while the effector moiety is capable of eliciting or modulating an immune response when administered to a host. The linker is selected to maintain the effector molecule in a proper position relative to the pathogen to permit interaction with the host's immune system when the hybrid molecule is bound to the pathogen.

The hybrid molecules of the present invention are used to "immunologically target" a wide variety of human and animal pathogens including viruses, bacteria, and protozoa. An exemplary list of pathogens which may be targeted is set forth in Table 1.

TABLE 1

| Pathogen | Binding Sugar[1] or other Moiety |
|---|---|
| VIRUSES: | |
| Influenza Virus | NeuAcα2→6Gal |
| | NeuAcα2→3Gal |
| Picornaviruses | Win compounds[2] |
| Polyoma Virus | NeuAcα2→6Gal |
| BACTERIA: | |
| *Escherichia coli* | |
| Type 1 | Man(α-glycosides) |
| Type P | Galα1→4Gal |
| Type S | NeuAcα2→3Gal |
| *Vibrio cholerae* | $Gm_3$ (ganglioside) |
| Actinomyces | Gal-X[3] |
| PROTOZOA: | |
| *Entamoeba histolytica* | Galβ1→4GlcNAc |
| *Plasmodium knowlesi* | Duffy antigen |
| *Plasmodium vivax* | Duffy antigen |

TABLE 1-continued

| Pathogen | Binding Sugar[1] or other Moiety |
|---|---|
| *Trypanosoma cruzi* | NeuAc[3] |

[1]NeuAc: N-acetylneuramic acid (sialic acid)
Gal: Galactose
GlcNAc: N-Acetylglucosamine
Man: Mannose
[2]Win compounds are described in Badger et al. (1988), supra., the disclosure of which is incorporated herein by reference. These compounds specifically bind to a pocket within the viral protein VP1 β-barrel structure and are useful as binding moieties in the compositions of the present invention.
[3]Exact structure undetermined.

The target pathogen may be any pathogen which has a receptor, preferably a conserved receptor, which binds to a cell surface ligand as part of the initiation of infection within that cell. The pathogen receptors are usually lectins but may also be other molecules, such as glycosidic enzymes, and the cell surface ligands are usually carbohydrates in the form of glycoproteins, glycolipids, oligosaccharides, and polysaccharides. Upon exposure to the pathogen, the binding moiety of the hybrid molecule will specifically attach to the pathogen receptor. The length and nature of the linker region permits the effector moiety to appear as an antigenic determinant of the pathogen itself. Thus, the pathogen will be processed by the host's immune system as if it naturally possessed the antigenic determinant defined by the effector moiety. The present invention is particularly useful for targeting pathogens having antigenic characteristics which vary over time, where the introduced antigenic determinant is invariant and can elicit or modulate a sustained immune response.

The hybrid molecules of the present invention will also be useful for binding and treating neoplastic cells based on binding of cell ligands to lectin receptors present on the neoplastic cells. Exemplary lectin receptors on neoplastic cells are responsible for binding to carbohydrate ligands on vascular endothelial cells, which is a necessary mechanism in the metastatic process. Thus, by employing binding moieties which mimic these cell-surface carbohydate ligands, present on the endothelial cells, the hybrid molecules can specifically attach to the neoplastic cells. A number of exemplary carbohydrate ligands and corresponding neoplastic cell receptors are identified in Raz et al. (1987) Can. Met. Rev. 6:433–452, the disclosure of which is incorporated herein by reference. Specific extracellular matrix adhesion molecules are described in McCarthy et al. (1985) Can. Met. Rev. 4:125–152; the cell-cell CAM adhesion system is described in Brackenbury (1985) Can. Met. Rev. 4:41–58; and the lymphocyte homing receptor system is described in Stoolman (1989) Cell 56:907–910, the disclosures of which are incorporated herein by reference.

The binding moiety will be selected to specifically bind to a receptor, usually a conserved receptor, on the pathogen or neoplastic cell of interest. The moiety will typically have a molecular weight below about 2 kD, usually being between about 2 kD and 400 daltons, preferably being between about 1.5 kD and 500 daltons, and will usually be other than a polypeptide or protein.

Most commonly, the binding moiety will be a carbohydrate comprising one or more sugars which are selected to mimic sugars, usually the terminal sugars, on the carbohydrate binding ligands on the cells infected by the pathogen (or attached by the neoplastic cell), usually being identical to the terminal residues which are bound during the infection or metastatic initiation process. Exemplary sugars include mannose, sialic acid, galactose, fucose, α-glucosamine, and derivatives thereof, usually linked through carbon rather than oxygen. Specific terminal sugars for a variety of pathogens are set forth in Table 1 above.

Other pathogens having such conserved carbohydrate ligands are described in the medical and scientific literature. See, for example, Cornfield et al., in *Sialic Acids*, Schauer, Ed., Springer-Verlag, New York, 1982. McGuire, in *Biological Roles of Sialic Acid*, Rosenberg and Schengrind, eds., plenum, New York, 1976; Sharon and Lis, *Lectins*, Chapman and Hall, London, 1989; and Mirelman, ed., *Microbial Lectins and Agglutinins: Properties and Biological Activity*, Wiley Series in Ecological and Applied Microbiology, Wiley-Interscience Publication, John Wiley and Sons, New York, 1986, the disclosures of which are incorporated herein by reference.

Carbohydrate binding moieties may be monovalent or multivalent and will usually comprise from one to eight sugars, more usually comprising from one to four sugars, and preferably comprising from one to two sugars, with the individual sugars being joined by the glycosidic linkages which are present in the natural carbohydrate ligand, i.e., maintaining the same stereochemistry, preferably employing carbon linkages instead of the oxygen linkages. Methods for synthesizing such saccharides and oligosaccharides are well described in the chemical literature. See, for example, Paulsen and Tietz (1985) Agnew. Chemie. Intl. Ed. Engl. 24:128; Toone et al. (1987) Tet. Lett. 44:5365–5422; Palcic et al. (1989) Carb. Res. 190:1–11; Sabesin et al. (1986) J. Am. Chem. Soc. 108:2068–2080; and Schmidt (1986) Agnew. Chemie. Intl. Ed. Engl. 25:212, the disclosures of which are incorporated herein by reference. A particular method for synthesizing a carbon-linked sialic acid (NeuAc) is described in detail in the Experimental section hereinafter.

In addition to carbohydrate binding moieties as just described, the present invention may employ other small synthetic moieties that have a adequate binding affinity and specificity to the conserved receptors on the pathogen or neoplastic cells of interest. In particular, the binding moiety (carbohydrate and non-carbohydrate) should have a binding affinity to the pathogen or cellular receptor of at least about 1 $mM^{-1}$ ($10^{-3}M^{-1}$), preferably being at least about 0.01 $mM^{-1}$ ($10^{-5}M^{-1}$), and more preferably being at least about 1 $\mu M^{-1}$ ($10^{-6}M^{-1}$).

The non-carbohydrate binding moieties will usually be other than a protein or polypeptide. Exemplary non-carbohydrate binding moieties include the Win compounds described in Badger et al. (1988) supra.

The identification of other compounds that can be employed as the binding moiety, i.e., those which are capable of binding to the pathogen receptor with the requisite affinity, can be achieved through the use of techniques known to those working in the area of drug design. Such methods include, but are not limited to, self-consistent field (SCF) analysis, configuration interaction (CI) analysis, and normal mode dynamics computer programs, all of which are readily available. See, Rein et al., *Computer-Assisted Modeling of Receptor-Ligand Interactions*, Alan Liss, New York, (1989).

Preparation of the identified compounds and moieties will depend on their structure and other characteristics and may normally be achieved by standard chemical synthesis techniques. See, for example, *Methods in Carbohydrate Chemistry*, Volumes I–VII: *Analysis and Prep-*

*aration of Sugars,* Whistler et al., eds, Academic Press, Inc., Orlando, 1962, the disclosure of which are incorporated herein by reference.

The effector moiety will be selected to provide a desired response or recognition by the host's immune system (usually humoral) when the moiety becomes attached to the pathogen or neoplastic cell as a result of the hybrid molecule binding to a receptor associated with the pathogen or cell. The effector moiety itself will frequently be a small compound, typically having a molecular weight below about 1 kD, preferably below about 500 D, usually in the range from about 100 to 400 D, and more usually in the range from about 250 to 350 D. Thus, the effector moiety will often be haptenic rather than antigenic, i.e., it will be unable to induce a primary immune response by itself but will be immunogenic when combined with the remainder of the hybrid molecule. Even small (haptenic) molecules will, however, induce a secondary or memory response in hosts who have been previously sensitized to the particular antigenic determinant.

Under certain circumstances, it may be desirable to employ larger compounds as the effector moiety, typically having molecular weights above about 1 kD, sometimes having molecular weights above about 1.5 kD, and occasionally having molecular weights above about 2 kD. Such antigenic compounds will usually be polypeptides or proteins, will usually be immunogenic by themselves (i.e., without binding to the remainder of the hybrid molecule) and may define more than one antigenic determinant site.

Antigenic determinants, sometimes referred to as epitopic sites or epitopes, are the portion of an antigenic or haptenic molecule that interacts with the host's immune system by molecular complementarity. In the humoral response, it reacts with cell surface Ig on B-cells to induce antibody production.

The antigenic determinant site(s) defined by the effector moiety will preferably be cross-reactive with an antigen or hapten to which the host has been previously sensitized. In this way, administration of the hybrid molecule to the host will evoke a secondary or memory response which will have a substantially immediate effect on the target pathogen or neoplastic cells. Alternatively, the effector moiety may be selected to introduce an antigenic determinant to which the host has not been previously exposed. In the latter case, the determinant will evoke a primary humoral response when administered to the host.

Exemplary effector moieties include those capable of producing a strong immunogenic response when administered to the host as part of the hybrid molecule, e.g., aminophenols, nitrophenols, fluorescent probes (fluroscein), phenolic glycosides (p-aminophenol-$\beta$-glycoside), and the like. Preferred effector moieties for which the host has a natural immunity include blood group carbohydrates, e.g., $\alpha$-D-GalNAc(1→3)$\beta$-D-Gal, $\alpha$-D-Galp-(1→3)-$\beta$-D-Gal, $\alpha$-D-GalpNAc-(1→3)-$\beta$-D-Gal, and $\alpha$-D-Galp-(1→3)-$\beta$-D-Galp-(1→3)-$\beta$-D-Gal; dinitrophenol (DNP); Gal$\alpha$1-3Gal; and the like.

A particularly preferred effector moiety is the Gal$\alpha$1→3Gal disaccharide for which most individuals have a natural immunity. The disaccharide and its properties are described in Galili et al. (1987) Proc. Natl. Acad. Sci. USA 84:1369-1373; Galili et al. (1987) J. Biol. Chem. 262:4683-4688; and Galili et al. (1986) J. Clin. Invest. 77:27-33, the disclosures of which are incorporated herein by reference. The Gal$\alpha$1→3Gal structure is preferred because it has been found that up to 1% of all circulating IgG in individuals is reactive with the disaccharide. The disaccharide can be prepared by chemical synthesis or by transfer of galactose using an appropriate glycosyltransferase to an acceptor molecule bearing a terminal galactosyl moiety. See, Larsen et al. (1989) Proc. Natl. Acad. Sci. USA 86:8227-8231, which describes a particular method for synthesizing the Gal$\alpha$1→3Gal disaccharide, the disclosure of which is incorporated herein by reference.

The hybrid molecule compositions of the present invention may also employ commonly used and commercially available compounds as the effector moiety. The use of biotin and fluoroscein effector moieties is described in detail in the Experimental section hereinafter.

While the effector moiety will most commonly provide for an invariant antigenic determinant, as described above, it is also possible that the effector moiety may be a drug or cytotoxic compound intended to kill or inhibit growth of the pathogen or neoplastic cell. Exemplary drugs and cytotoxic agents include antibacterial drugs; anti-neoplastic drugs; photoactivated compounds; radionuclides; toxin A chains, such as ricin A chain and abrin A chain; and the like.

While the hybrid molecule compounds of the present invention will find their greatest use in antigenic targeting of pathogens and neoplastic cells, they may also be used for the detection of pathogens or neoplastic cells in in vitro assays. The use of both biotin and fluoroscein effector moieties is particularly convenient for in vitro assays as both biotin and fluoroscein are well known reporter molecules for which a wide variety of detection systems exist.

The linking region or group is selected to provide the necessary covalent bridge between the binding moiety and the effector moiety. Frequently, the linking region will be derived from a bifunctional compound having a reactive group at one end which is capable of binding to the binding moiety and a second reactive group which is capable of binding to the effector moiety. Alternatively, the linking region may be synthesized together with either the binding moiety or the effector moiety and will then include only a single reactive functionality for covalent binding to the other moiety.

The nature of the linking region is not critical, but it should provide a sufficient spacing and flexibility between the binding moiety and the effector moiety so that the effector moiety is sufficiently exposed on the surface of the pathogen to interact with the host's immune system in a desired manner. The length of the linking region will usually be between about 10 Å and 40 Å, preferably being between about 15 Å and 30 Å. The linking region should be resistant to degradation when administered to a host as part of a hybrid molecule and should further not contribute to non-specific adhesion of the hybrid molecule, i.e., adhesion or binding to other than the target receptor. It will be appreciated that the hybrid molecules of the present invention should bind with a high affinity and specificity to only the pathogen of interest.

The carbohydrate binding moieties will preferably be attached to the other portions of the hybrid molecule through carbon bonds. While natural glycosidic linkages occur through an oxygen (O-glycosidic bonds), the hybrid molecules of the present invention preferably employ carbon-glycosidic bonds to promote stability and inhibit chemical and enzymatic hydrolysis. Specific syntheses techniques for preparing such C-linked glycosides are set forth in the Experimental section hereinafter.

Exemplary bifunctional compounds which can be used for attaching carbohydrate moieties to effector moieties include bifunctional polyethylene glycols, polyamides, polyethers, polyesters, and the like. General approaches for linking carbohydrate moieties to other small molecules, polypeptides, and the like, are well described in the chemical literature. See, for example, Lee et al. (1989) Biochemistry 28:1856 (carbohydrate conjugation); Bhatia et al. (1989) Anal. Biochem. 178:408 (protein conjugation); Janda et al. (1990) J. Am. Chem. Soc. 112:8886 (protein conjugation), the disclosures of which are incorporated herein by reference.

The hybrid molecules of the present invention can be incorporated as components of pharmaceutical compositions useful to attenuate, inhibit, prevent, or otherwise treat pathogenic infections or neoplastic disease. The pharmaceutical compositions should contain a therapeutic or prophylactic amount of at least one hybrid molecule according to the present invention present in a pharmaceutically-acceptable carrier. The pharmaceutically-acceptable carrier can be any compatible, non-toxic substance suitable to deliver the hybrid molecules to an intended host. Sterile water, alcohol, fats, waxes, and inert solids may be used as the carrier. Pharmaceutically-acceptable adjuvants, buffering agents, dispersing agents, and the like, may also be incorporated into the pharmaceutical compositions. The preparation of pharmaceutical compositions incorporating active agents is well described in the medical and scientific literature, see, for example, *Remington's Pharmaceutical Sciences*, Mack Publishing Company, Easton, Pa., 16th Ed., 1982, the disclosure of which is incorporated herein by reference.

The pharmaceutical compositions just described are suitable for systemic administration to the host, including both parental and oral administration. Preferably, the pharmaceutical compositions will be administered parenterally, i.e., subcutaneously, intramuscularly, or intravenously. Thus, the present invention provides compositions for administration to a host, where the compositions comprise a pharmaceutically-acceptable solution of the hybrid molecules in an acceptable carrier, as described above.

The concentration of the hybrid molecules in the pharmaceutical compositions may vary widely, i.e., from less than about 0.1 % by weight of the pharmaceutical composition to about 20% by weight, or greater. A typical pharmaceutical composition for intramuscular injection would be made up to contain, for example, 1 to 4 ml of sterile buffered water and 1 $\mu$g to 1 mg of the hybrid molecule in the present invention. A typical composition for intravenous infusion could be made up to contain 100 to 500 ml of sterile Ringer's solution and about 1 to 100 mg of the hybrid molecule.

The pharmaceutical compositions of the present invention can be administered for prophylactic and/or therapeutic treatment of pathogenic infection. In therapeutic applications, the pharmaceutical compositions are administered to a host already infected with the pathogen. The pharmaceutical compositions will be administered in an amount sufficient to bind to at least a substantial portion of the population of viable pathogens present in the host. An amount adequate to accomplish this is defined as a "therapeutically effective dose." Such effective dose will depend on the severity of the infection and on the general state of the patient's own immune system, but will generally range from about 0.01 $\mu$g to 10 mg of the hybrid molecule per kilogram of body weight of the host, with dosages of from about 0.1 $\mu$g to 1 mg/kg being more commonly employed. In life-threatening situations, it may be desirable to administer dosages substantially exceeding those set forth above.

For prophylactic applications, the pharmaceutical compositions of the present invention are administered to a host not already infected by the pathogen, but perhaps recently exposed to or thought to have been exposed to, or at risk of being exposed to the pathogen. The hybrid molecules will then be able to block initial infection of the patient cells by the pathogen as well as being able to elicit an immune response directly against the pathogen which may be present. The amount of hybrid molecule required for this purpose, referred to as a prophylactically-effective dosage, are generally the same as described above for therapeutic treatment.

For the treatment of neoplastic disease, the pharmaceutical compositions may be formulated generally as described above. The dosages and frequency of administration will depend heavily on the stage of disease, the prognosis, evidence of metastasis, and the like. Frequently, treatment will be performed in combination with other modalities, such as surgery, radiation treatment, administration of other chemotherapeutic drugs, and the like.

The following examples are offered by way of illustration, not by way of limitation.

EXPERIMENTAL

Figure 2:
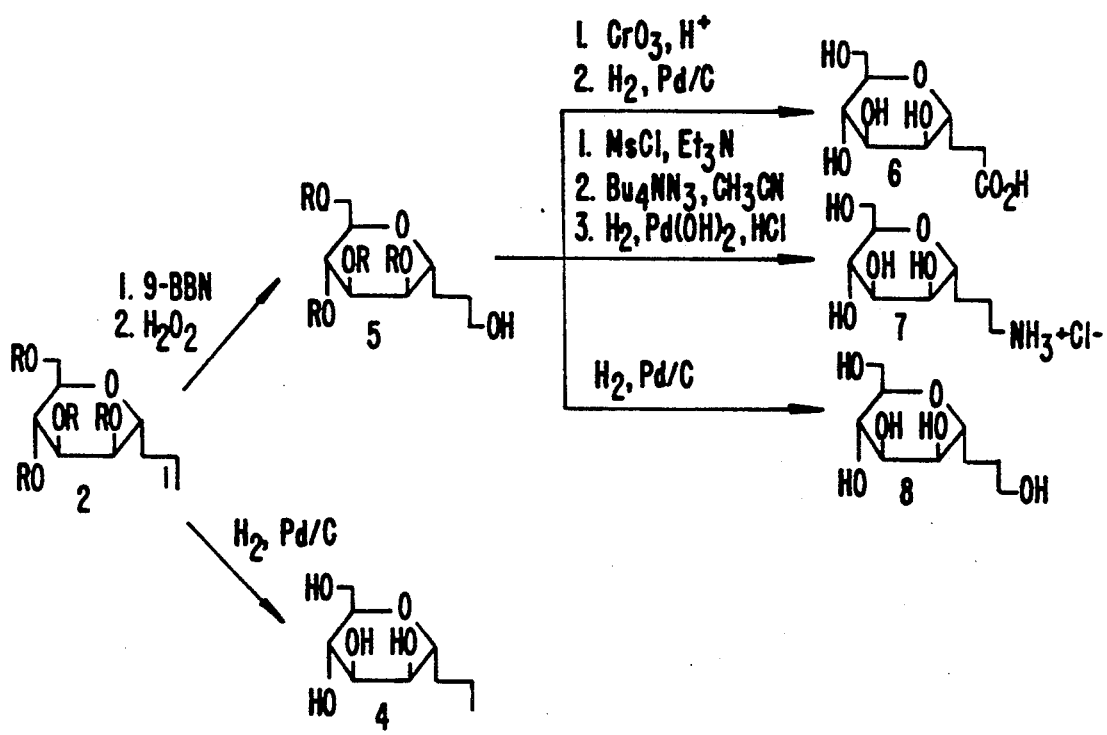

C-glycosides were synthesized as outlined in FIGS. 1–4. Methyl (2,3,4,6-tetra-O-benzyl)-$\alpha$-D-mannopyranoside 1 was treated with allyltrimethylsilane in acetonitrile using trimethylsilyl triflate (TMSOTf) as a catalyst according to conditions reported by Hosomi et al. (1984) Tetrahedron Lett. 25:2383; Hosome et al. (1987) Carbohydrate Research 171:223 (FIG. 1). The C-glycosides 2 and 3 were obtained in a greater than 15:1 mixture in an overall yield of 91%. Compound 2 was deprotected and reduced by hydrogenolysis ($H_2$, Pd/C) to give alkane 4 (FIG. 2.).

Figure 3:
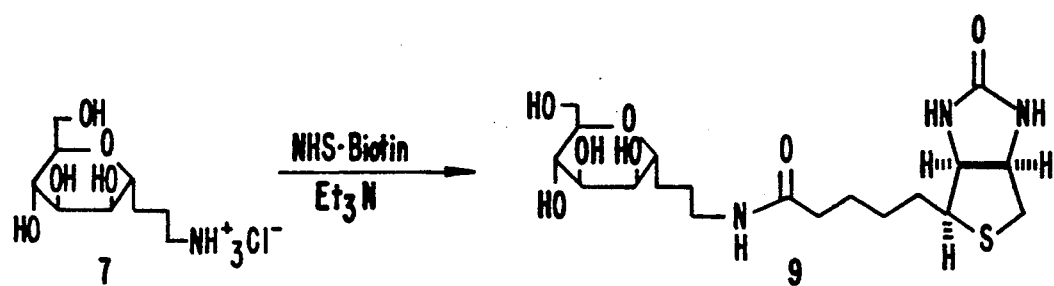
Figure 4:
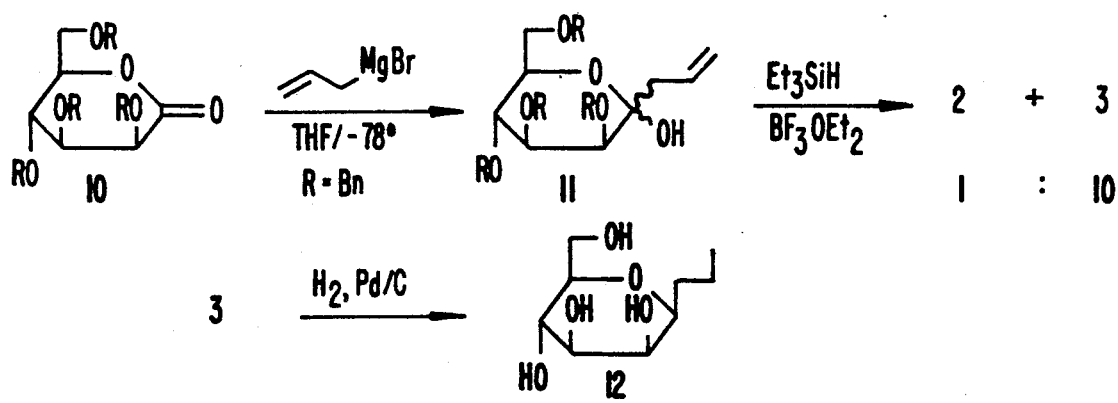

Compounds 6–8 were synthesized from alcohol 5 which was obtained by hydroboration (9-BBN) of compound 2. Oxidation of alcohol 5 using Jones' reagent ($CrO_3$, $H_2SO_4$) followed by hydrogenolysis ($H_2$, Pd/C) gave the free acid 6. The amine hydrochloride salt 7 was synthesized from compound 5 by mesylation of the primary alcohol (MsCl, $Et_3N$) followed by azide displacement (nBu$_4$NN$_3$, $CH_3CN$) (Brandstrom et al. (1974) Acta Chem. Scand. B 28:699) and hydrogenolysis ($H_2$, Pd(OH)$_2$, HCl). Debenzylation ($H_2$, Pd/C) of compound 5 directly gave alcohol 8. Reaction of compound 7 with N-hydroxysuccinimidobiotin and $Et_3N$ in 1:1 DMF/MeOH gave conjugate 9 (FIG. 3).

It has been reported that $\beta$-O-glycosides of mannose do not bind to *E. coli* type 1 pili receptors (Firon et al. (1984) Infection and Immunity 43:1088). Therefore, as a control for the cell-surface binding studies, we synthesized by $\beta$-C-glycoside 3 using a modification of a procedure developed by Lewis et al. (FIG. 4) (Lewis et al. (1982) J. Am. Chem. Sic. 104:4976). The addition of allylmagnesium bromide to lactone 10 (Lactone 10 was synthesized from methyl (2,3,4,6-tetra-O-benzyl)-$\alpha$-D-mannopyranoside by hydrolysis of the methyl glycoside (AcOH, $H_2O$) followed by Jones' oxidation ($CrO_3$/H-

2SO4) in acetone.) gave hemiketal 11 as a mixture of anomers. Stereoselective reduction using triethylsilane and boron trifluoride etherate (Et$_2$SiH, BF$_3$OEt$_2$) in acetonitrile gave a 1:10 mixture of C-glycosides 2 and 3. Compound 3 was deprotected and reduced by hydrogenolysis to give alkane 12.

Compounds 4, 6–9 and 12 were assayed for bacterial receptor binding using agglutination studies with yeast cells and their inhibitory activity was compared to that of methyl α-D-mannopyranoside 13 (Firon et al. (1983) Carbohydrate Research 120:235; Eshdat et al. (1978) Biochem. Biophys. Res. Commun. 85:1551; and Firon et al. (1982) Biochem. Biophys. Res. Commun. 105:1426. The bacterial strain used in our study was a systemically invasive *E. coli* K1 pilA+::tetR strain that is responsible for sepsis and meningitis in human infants (Bloch et al. (1990) Infection and Immunity 58:275). A summary of the results is given in Table 2.

TABLE 2

Inhibitory Activity of C-Glycosides of Mannose on the Bacterial Receptor-Mediated Agglutination of Yeast Cells.[a]

| Entry | Compound | Concentration (mM)[b] | Relative Inhibitory Activity[c] |
|---|---|---|---|
| 1 | 13 | 67 | 1 |
| 2 | 6 | 47 | 1.4 |
| 3 | 7 | 40 | 1.7 |
| 4 | 8 | 13 | 5.2 |
| 5 | 4 | 7 | 9.6 |
| 6 | 9 | 7 | 9.6 |

TABLE 2-continued

Inhibitory Activity of C-Glycosides of Mannose on the Bacterial Receptor-Mediated Agglutination of Yeast Cells.[a]

| Entry | Compound | Concentration (mM)[b] | Relative Inhibitory Activity[c] |
|---|---|---|---|
| 7 | 14 (mannose C-glycoside linked to p-nitrophenyl ether) | 1.6 | 42 |
| 8 | mannose C-glycoside-biotin conjugate + Streptavidin | 0.6 mM[d] | — |
| 9 | mannose C-glycoside-biotin conjugate + Avidin | 0.05 mM (50 μM) | 1340 |

[a]*E. coli* K1 pilA+::tetR were grown for 24 h at 37° C. on solid LB media supplemented with tetracycline and were suspended with a cotton swab in 4 mL of Dulbecco's PBS to a final dilution of 2 × 10⁸ cells/mL. Yeast (*Saccharomyces cerevisiae*, wild type) were grown for 36 h on solid YPD media at 30° C. and were suspended with a cotton swab in 4 mL of Dulbecco's PBS to a final dilution of 1 × 10⁸ cells mL. Protein concentrations were determined by BCA Protein Assay (Pierce). Agglutination assays were performed on a 20 well ceramic ring plate. Typically, 90 μl of a solution of the test compound was combined with 30 μl of the bacterial suspension. After 30 seconds, 30 μl of the yeast suspension was added to give a final volume of 150 μl and the wells were allowed to develop for 3 min. with agitation. A 5 μl aliquot was removed from each well and spread onto a standard microscope slide. The slides were quickly heat fixed and mounted with 10 μl of glycerol. The slides were examined under phase contrast at 500× magnification using a Zeiss Axioskip microscope. Agglutination was observed as clusters of cells. total inhibition of agglutination was determined by the observation of single cells only.
[b]Concentration causing total inhibition of yeast agglutination.
[c]These numbers represent the concentration of methyl α-D-mannopyranoside divided by the concentrations listed in column 3.
[d]Only partial inhibition of agglutination was achieved at this concentration.

Three important conclusions can be drawn from these data: (1) Carbon-linked glycosides bind to bacterial mannose lectines and inhibit the attachment of *E. coli* K1cells to yeast. Since the 28 kD lectin is highly conserved in its morphology as determined by its cross reactivity with monoclonal and polyclonal antibodies (Hanson et al. (1988) Nature 332:265), these compounds should also bind to other type 1 pili receptors. The β-C-glycoside 12 shows no inhibitory activity at a concentration of 100 mM, demonstrating that the α-specificity of the receptor observed with O-glycoisides is maintained among C-glycosides. (2) The binding of C-glycosides is stronger than that of methyl α-D-mannopyranoside 13. The increase in binding affinity seems to be a function of the hydrophobicity of the carbon-linked side chain. For example, compare the charged compounds 6 and 7 (entries 2 and 3) with the neutral, hydrophobic compounds 4 and 9 (entries 5 and 6). Compounds 4 and 9 inhibit agglutination at a concentration that is approximately one order of magnitude less than that of the charged compounds 6 and 7. It is believed that the poor solvation of the hydrophobic side chain in water increases the affinity of compounds 4 and 9 for the relatively hydrophobic receptor binding site. This "hydrophobic effect" has also been observed with oxygen-linked glycosides such as compound 14 (entry 7) (Firon et al. (1982) supra.).

Finally, it was observed an increase in binding affinity for the biotin-streptavidin (avidin) system (entries 8 and 9, Table 2). Unfortunately, streptavidin has limited solubility under the conditions of the assay. Despite the apparent increase in affinity of the conjugate of streptavidin and compound 9, total inhibition was not achieved at this concentration (entry 8). Avidin, a more soluble protein, was therefore used in place of streptavidin. It was observed that avidin alone has an intrinsic affinity for the receptor binding site which is probably due to its glycosylation pattern (total inhibition of agglutination by avidin is achieved at a concentration of 0.4 mM (Huang et al. (1971) J. Biol. Chem. 246:686)). However, the conjugate of avidin with compound 9 (entry 9) inhibits agglutination at a concentration of 0.05 mM (50 μM), an order of magnitude less than avidin alone, and was the tightest binding C-glycoside conjugate in our study. This effect was believed to be due to the tetravalency of the biotin-avidin complex. Biotinylation of ligands that bind to cell-surface receptors can be used as a general approach to create multivalent ligand arrays with control over their spacial arrangement.

The biotin-avidin system also allowed targeting molecules to the surface of pathogenic organisms. Since the binding of the conjugate alters the antigenic properties of the bacterial surface, the strategy can be used to target anti-avidin antibodies to the pathogen that would not otherwise recognize the organism.

Figure 5:
Figure 6:
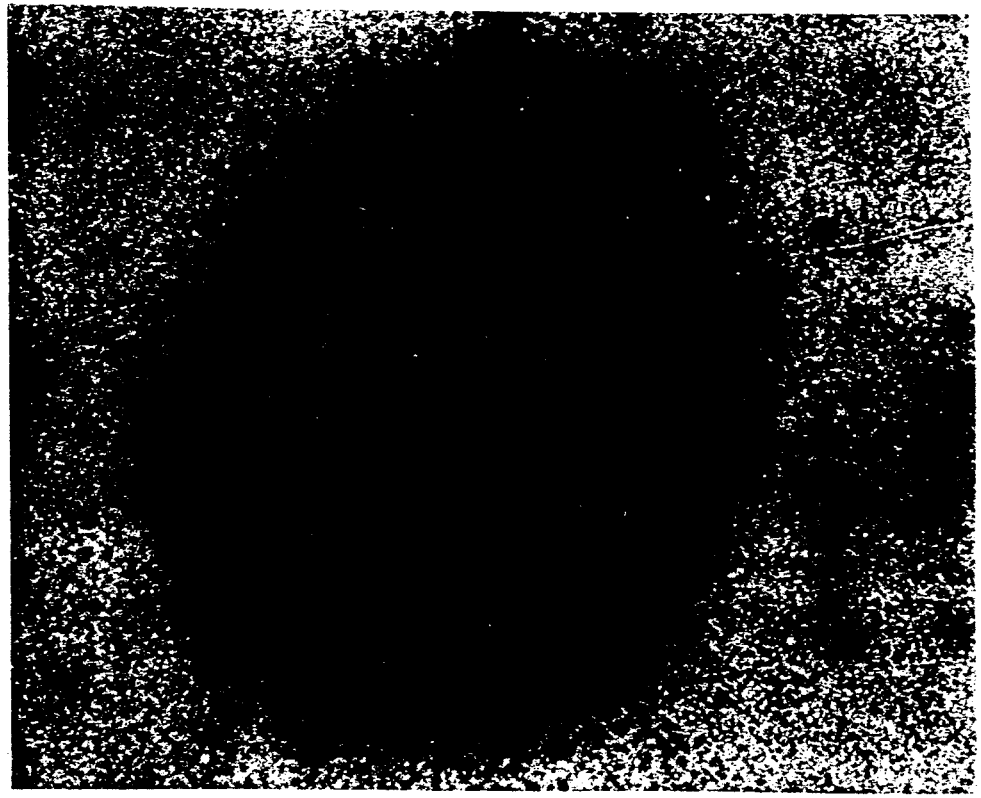

E coli cells bound with avidin, as described above, were sequentially exposed to anti-avidin antibodies and gold (15 nm) colloidal particles bound to protein A. It was expected that the gold would localize on the E. coli cell surface through an antibody-protein A bridge. Localization on bacterial pili was confirmed by transmission electron microscopy (TEM). The results are shown in FIG. 5 (typical gold particle shown by arrow) and FIG. 6 (control where E. coli cells incubated with protein A-gold without anti-avidin antibody).

Binding of complement (Clq) to anti-avidin (IgG2) bound to E. coli through the biotin-mannose hybrid molecule has also been shown. Clq binding is the first step in the complement cascase which is part of the humoral response.

Figure 7:
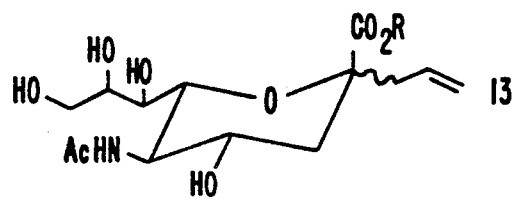
Figure 8:
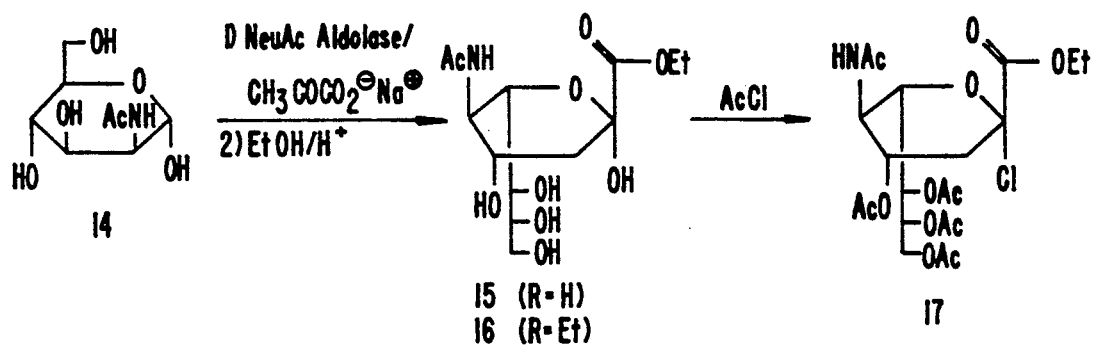
Figure 9:
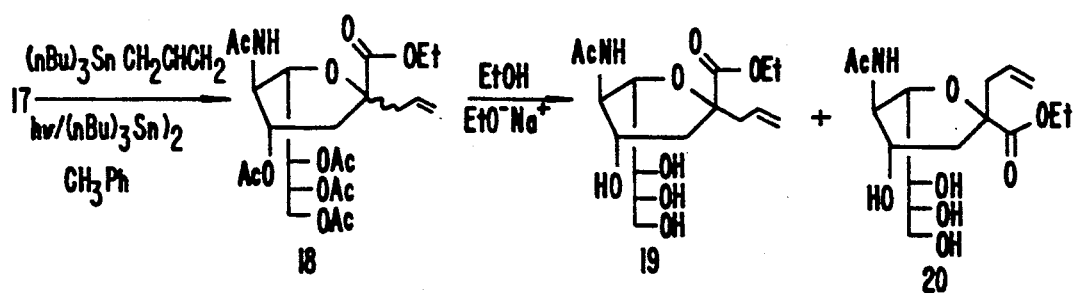

A stable non-hydrolyzable analog of sialic acid 13 (FIG. 7) was synthesized as follows. The compound is a carbon glycoside of NeuAc prepared by a combined chemical enzymatic approach.

Several methods for the synthesis of carbon glycoside (C-glycosides) have been reported. See, Crich and Lim, (1990) Tet. Lett. 31:1897; Nicotra et al. (1987) J. Org. Chem. 52:5627; Hosomi et al. (1984) Tet. Lett. 25:2383; and Norbeck et al. (1987) J. Org. Chem. 52:2174. In our hands, many of these methods failed to give C-glycosides of N-acetyl neuraminic acid under a variety of conditions. Problems associated with Lewis-acid catalyzed methods exist due to the carboxylate. Approaches that require basic conditions fail because of a variety of unwanted side reactions. The use of radical coupling reactions eliminates these problems.

The key radical species required for C-glycoside synthesis is generated under mild conditions and on a carbon atom that can be stabilized by the adjacent carboxylate group and oxygen atom attached to it (capadative radical). Schmidt et al., for example, has shown that methyl-2-deoxy-2-$\beta$-chloro-4,7,8,9-tetra-O-acetyl-N-acetyl-neuraminate can readily be reduced using tributyl tin hydride (Schmidt et al. (1988) Tet. Lett. _:3643. Towards this end the ethyl ester of neuraminic acid (Compound 4) was synthesized by an enzyme catalyzed aldol reaction using NeuAc aldolase between N-acetyl mannosamine (Hosomi et al. (1984) Tet. Lett. 25:2382) and sodium pyruvate to give NeuAc 3 (Bednarski et al. (1988) J. Amer. Chem. Soc. 110:7159; Auge et al. (1984) Tet. Lett. 25:4663; and Kim et al. (1988)). Treatment of the crude reaction mixture with hydrogen chloride gas in ethanol gives the ethyl ester which can be purified by silica gel chromatography. The data for this compound has been reported in Eschenfelder and Brossmer (1975), Tet. Lett. 35:3069. Treatment of compound (Norbeck et al. (1987) J. Org. Chem. 52:2174) with acetyl chloride at room temperature for 24 h gives the glycosyl chloride 16.

Compound 17 was then treated with allyl tributyltin and a catalytic amount of bis (tributyltin) and photolyzed for 18 h using a 450 Watt Hanovia lamp with a pyrex filter to give approximately a 1:1 mixture of the C-glycosides 18 and 19 which were deprotected using sodium ethoxide in aqueous ethanol yielding 19 and 20 which could easily be separated by silica gel chromatography. Compound 19 (the less polar isomer) is assigned to be the $\alpha$-anomer in which the carboxylate group is axial; compound 20 (the more polar isomer) is assigned to be the $\beta$-anomer. The stereochemical assignment is based on analogous compounds and NOE studies.

Detailed synthesis methods for each of the compounds described in the Experimental section are contained in the Appendix to this application.

Although the foregoing invention has been described in detail for purposes of clarity of understanding, it will be obvious that certain modifications may be practiced within the scope of the appended claims.

What is claimed is:

1. A method for introducing a heterologous antigenic determinant to the surface of a pathogen or cell, said method comprising exposing the pathogen or cell to hybrid molecules having a carbohydrate binding moiety which binds specifically to a conserved pathogen or cellular receptor and an effector moiety which includes the heterologous antigenic determinant, wherein the heterologous antigenic determinant is exposed when the binding moiety is bound to the receptor and wherein the hybrid molecule has a molecular weight below about 3 kD.

2. A method as in claim 1, wherein the carbohydrate binding moiety terminates in at least one carbon-linked sugar.

3. A method as in claim 2, wherein the carbon-linked sugar is selected from the group consisting of mannose, sialic acid, galactose, fucose, $\alpha$-glucoseamine, galactosamine, and derivatives thereof.

4. A method as in claim 2, wherein the receptor is a conserved pathogen receptor which mediates attachment of the pathogen to susceptible cells.

5. A method as in claim 1, wherein the receptor is a conserved cellular receptor which mediates metastatic attachment of a neoplastic cell.

6. A method as in claim 1, wherein the pathogen is a viral pathogen selected from the group consisting of influenza viruses, picornaviruses, and papilloma viruses.

7. A method as in claim 1, wherein the pathogen is a bacteria selected from the group consisting of *Escherichia coli*, and *Vibrio cholerae*.

8. A method as in claim 1, wherein the pathogen is a protozoa selected from the group consisting of *Entamoeba histolytica*, *Plasmodium knowlesi*, *Plasmodium vivax*, and *Trypanosoma cruzii*.

9. A method as in claim 1, wherein the binding moiety will bind to the pathogen with an affinity of at least about 1 mM$^{-1}$.

10. A method as in claim 1, wherein the hybrid molecule further comprises a linking region which joins the carbohydrate binding moiety to the effector moiety.

11. A method as in claim 10, wherein the linking region is water soluble and has a length in the range from about 10 Å to 40 Å.

12. A method for introducing a heterologous antigenic determinant to a lectin on the surface of a pathogen, said method comprising:
exposing the pathogen to hybrid molecules including (1) a carbohydrate binding moiety which terminates in at least one carbon-linked sugar and which binds specifically to the surface lectin, (2) an effector moiety which includes the heterologous antigenic determinant, wherein the determinant is exposed when the binding moiety is bound to the lectin, and (3) a linker region which joins the carbohydrate binding moiety to the effector moiety, wherein the linker region is water soluble and substantially free from non-specific cellular binding.

13. A method as in claim 12, wherein the hybrid molecule has a molecular weight below about 3 kD.

14. A method as in claim 12, wherein the carbohydrate binding moiety binds to the surface lectin with a affinity of at least about 1 mM$^{-1}$.

15. A method as in claim 12, wherein the carbon-linked sugar is selected from the group consisting of mannose, sialic acid, galactose, fucose, α-glucoseamine, galactosamine, and derivatives thereof.

16. A method as in claim 12, wherein effector moiety has a molecular weight below about 1000 D.

17. A method as in claim 16, wherein the effector moiety is selected from the group consisting of blood group carbohydrates, dinitrophenol, and Galα1→3Gal.

18. A method as in claim 17, wherein the binding moiety is sialic acid and the effector moiety is Galα1→3Gal.

19. A method as in claim 12, wherein the linking region has a length in the range from 10 Å to 40 Å.

* * * * *